United States Patent [19]

Konomura et al.

[11] 4,449,518

[45] May 22, 1984

[54] DISINFECTION INDICATOR FOR MEDICAL EQUIPMENT

[75] Inventors: Yutaka Konomura; Yasuhiko Omagari, both of Tokyo, Japan

[73] Assignee: Olympus Optical Co., Ltd., Tokyo, Japan

[21] Appl. No.: 364,972

[22] Filed: Apr. 2, 1982

[30] Foreign Application Priority Data

Apr. 13, 1981 [JP] Japan .................. 56-55407
Apr. 13, 1981 [JP] Japan .................. 56-55408
Apr. 13, 1981 [JP] Japan .................. 56-55409
Apr. 13, 1981 [JP] Japan .................. 56-55410
Apr. 13, 1981 [JP] Japan .................. 56-55411

[51] Int. Cl.³ .............. A61B 17/00; G01L 5/00; G01K 1/02
[52] U.S. Cl. .................. 128/4; 73/862.53; 116/216; 128/303 R; 128/736; 374/187
[58] Field of Search .............. 116/216, 218; 374/150; 422/119; 128/736, 4, 303 R; 436/147

[56] References Cited

U.S. PATENT DOCUMENTS

| 3,440,997 | 4/1969 | Rogen et al. | 116/216 |
| 3,483,752 | 12/1969 | Rogen et al. | 116/216 |
| 3,516,082 | 6/1970 | Cooper | 337/382 X |
| 3,853,546 | 12/1974 | Werner et al. | 73/862.53 |
| 4,043,323 | 8/1977 | Komiya | 128/4 |
| 4,066,082 | 1/1978 | Arcan et al. | 128/303 R |
| 4,251,719 | 2/1981 | Ryder | 422/119 X |

Primary Examiner—Daniel M. Yasich

[57] ABSTRACT

A disinfection indicator mounted on medical equipment which is inserted into a channel for forceps and repeatedly used after thermal sterilization, includes a deformable portion, made of a shape memory alloy having a one-way shape memory effect, which is deformed plastically by an external force, from a shape indicating disinfection of the medical equipment to a predetermined original shape when the medical equipment is in use, and which is modified from the original shape to the shape indicating disinfection of the medical equipment when the medical equipment is heated to a temperature higher than a predetermined temperature.

10 Claims, 36 Drawing Figures

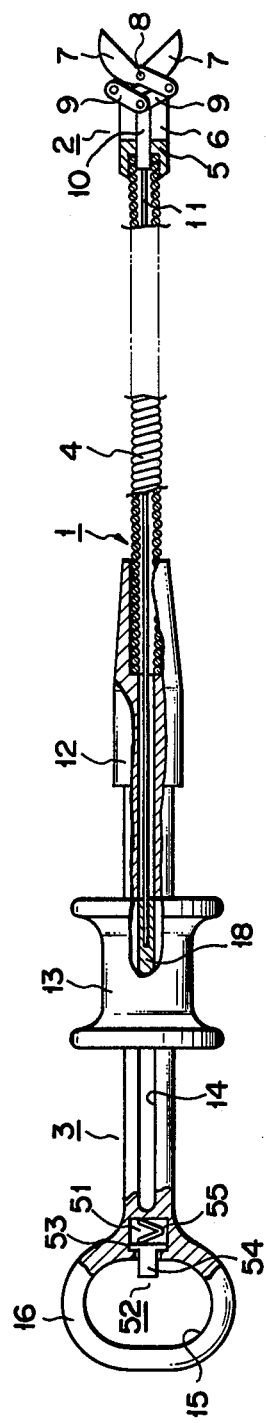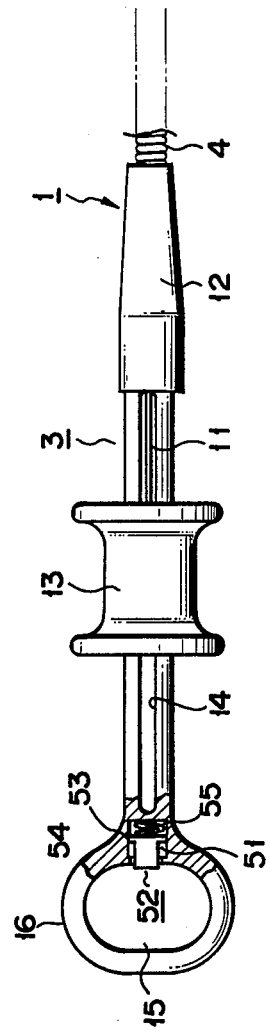
FIG. 9
FIG. 10

DISINFECTION INDICATOR FOR MEDICAL EQUIPMENT

BACKGROUND OF THE INVENTION

The present invention relates to a disinfection indicator for indicating whether or not medical equipment which is to be repeatedly used has been disinfected by thermal sterilization or steam sterilization.

SUMMARY OF THE INVENTION

The present invention has for its object to provide a disinfection indicator for medical equipment which has a simple structure and is manufactured simply, and which is mounted easily to medical equipment and only requires a small mounting space.

A deformation portion of a disinfection indicator for medical equipment according to the present invention is plastically deformed from a shape which indicates disinfection of medical equipment to another shape by an external force when it is used. When the disinfection indicator is heated to a predetermined temperature or higher when medical equipment is thermally disinfected, the deformable portion of the indicator returns from the first shape to a second shape which visually indicates disinfection of the medical equipment. This deformable portion is made of a shape memory alloy which shows a one-way shape memory effect.

Medical equipment according to the present invention are medical instruments which are repeatedly used after thermal disinfection. They are, for example, an endoscope, instruments for assisting insertion of the endoscope, supplementary instruments of the endoscope, and laser surgical knives.

Disinfection may be detected directly by the shape of the deformable portion of the disinfection indicator. Alternatively, disinfection may be detected by an indicating member which is moved by the deformable portion.

BRIEF DESCRIPTION OF THE DRAWINGS

FIGS. 1 and 2 show a disinfection indicator of medical equipment according to one embodiment of the present invention, in which FIG. 1 is a partially cutaway side view thereof and FIG. 2 is a partial side view in a condition different from the view of FIG. 1;

FIGS. 3 to 5 show a disinfection indicator of medical equipment according to a second embodiment of the present invention, in which FIG. 3 is a perspective view thereof, FIG. 4 is a partial sectional view thereof, and FIG. 5 is a partial sectional view when the medical equipment is in operation;

FIGS. 6 to 8 show a disinfection indicator of medical equipment according to a third embodiment of the present invention, in which FIG. 6 is a perspective view thereof, FIG. 7 is a partially enlarged perspective view thereof, and FIG. 8 is a partially enlarged perspective view in a condition different from the view of FIG. 7;

FIGS. 9 and 10 show a disinfection indicator of medical equipment according a fourth embodiment of the present invention, in which FIG. 9 is a partially cutaway side view thereof, and FIG. 10 is a partially cutaway side view in a condition different from the view of FIG. 9;

FIGS. 11 to 13 show a disinfection indicator of medical equipment according to a fifth embodiment of the present invention, in which FIG. 11 is a partially cutaway side view thereof and FIGS. 12 and 13 are partially cutaway enlarged side views thereof in different operating conditions;

FIGS. 14 and 15 show a disinfection indicator of medical equipment according to a sixth embodiment of the present invention, in which FIGS. 14 and 15 are sectional views in different operating conditions;

FIGS. 16 and 17 show a disinfection indicator of medical equipment according to a seventh embodiment of the present invention, in which FIG. 16 is a partially cutaway side view of the overall disinfection indicator, and FIG. 17 is a side view in an operating condition different from the view of FIG. 16;

FIGS. 19 to 21 show a disinfection indicator of medical equipment according to a ninth embodiment of the present invention, in which FIG. 19 is a longitudinal sectional view of a patient when the medical equipment is being used, FIG. 20 is a plan view showing part of the medical equipment, and FIG. 21 is a partial longitudinal sectional view of the medical equipment;

FIGS. 22 to 24 show a disinfection indicator of medical equipment according to a tenth embodiment of the present invention, in which FIG. 22 is a longitudinal sectional view thereof, and FIGS. 23 and 24 are views showing different operating conditions thereof;

FIGS. 26 to 28 show a disinfection indicator of medical equipment according to an eleventh embodiment of the present invention, in which FIG. 26 is a perspective view thereof, FIG. 27 is a partially cutaway side view thereof, and FIG. 28 is a partially cutaway side view thereof when it is used;

FIGS. 29 to 31 show a disinfection indicator of medical equipment according to a twelfth embodiment of the present invention, in which FIG. 29 is a side view when it is used, and FIGS. 30 and 31 are partially cutaway views in different operating conditions;

FIGS. 34 to 36 show still another modification of the disinfection indicator for medical equipment of FIG. 29 according to the present invention, in which FIG. 34 is a front view thereof, and FIGS. 35 and 36 are sectional views in different operating conditions.

DETAILED DESCRIPTION OF THE PREFERRED EMBODIMENTS

Figure 1:
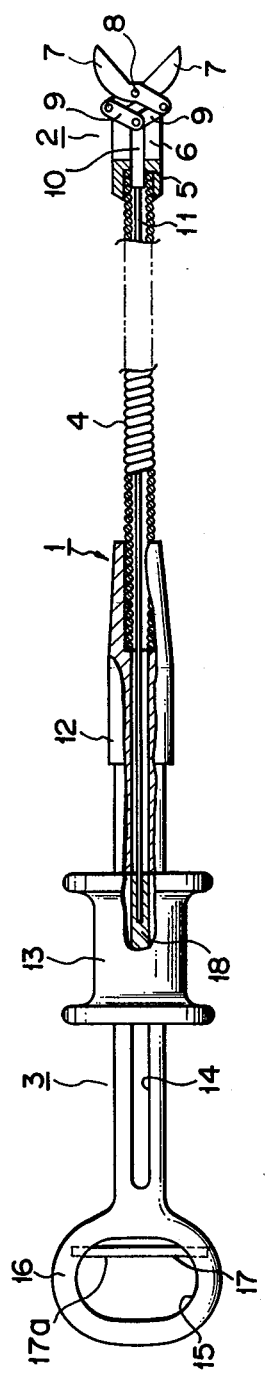
Figure 2:
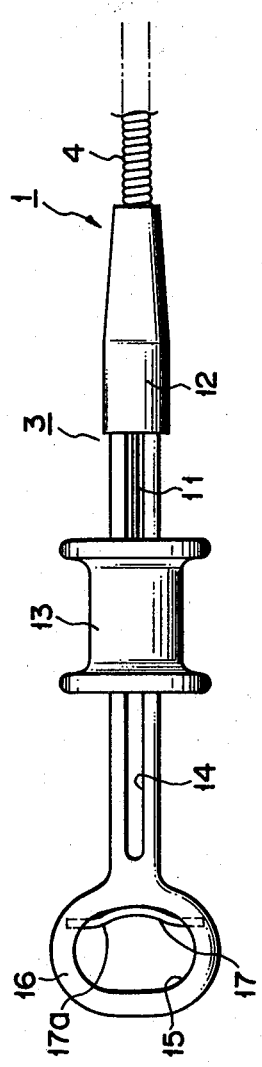

Various types of disinfection indicators according to embodiments of the present invention will be described with reference to the accompanying drawings. FIGS. 1 and 2 show a disinfection indicator according to a first embodiment of the present invention. Reference numeral 1 denotes instrument main body (medical equipment) for an endoscope which is inserted into a channel for forceps. A treatment part 2 is formed at the top of the instrument main body 1. An operation part 3 is formed at the base of the instrument main body 1. An insertion member 4 of a flexible tube is disposed between the treatment part 2 and the operation part 3. A support member 5 of a tubular shape is disposed at the treatment part 2. The base of the support member 5 is mounted on the top of the insertion member 4. A cut groove 6 is formed at the top of the support member 5. A pair of treatment members 7 are pivotal about a pin 8 in the cut groove 6. Each base of the treatment members 7 is mounted so as to be pivotal about one end of each of arms 9. The other end of each of the arms 9 is pivotal about the top of a push bar 10. The push bar 10 is free to move reciprocally inside the support member 5. The base of the push bar 10 is mounted to one end of an operation wire 11 which is free to move reciprocally inside the insertion member 4.

On the other hand, the operation part 3 comprises an operation main body 12 and a slider 13. The base of the insertion member 4 is mounted to the operation main body 12. Further, an elongate groove 14 which communicates with the insertion member 4 is formed in the operation main body 12. A finger insertion part 16 having a finger insertion hole 15 which is sufficiently larger than a finger is formed at the operation main body 12. A deformable portion 17a of a disinfection indicator of a rod shape is hooked across the finger insertion hole 15. Both ends of the disinfection indicator 17 are mounted inside the finger inserting part 16. The disinfection indicator 17, for example, consists of a Cu-Zn-Al (73%-20%-7%) alloy. The indicator 17 may be made by other alloys such as Ti-Ni (50%-50%) alloy, Cu-Al-Ni alloy, Cu-Al alloy, Au-Cd alloy, Ni-Al alloy, Cu-Zn alloy, etc. When the disinfection indicator 17 is heated to a temperature of 50° to 100° C. or higher by thermal sterilization, the crystal structure of the disinfection indicator 17 is modified from a martensite phase to a mother phase (reverse modification). This alloy has a one-way shape memory effect. When the crystal structure of the shape memory alloy of the disinfection indicator 17 is in the mother phase (high temperature phase), the deformable portion 17a of the disinfection indicator 17 is restored from an initial curved shape as shown in FIG. 2 to a linear shape, as shown in FIG. 1. This linear shape is an disinfected indicating shape and indicates that medical equipment has been disinfected. The slider 13 is mounted to the operation main body 12 to be slidable along the elongate groove 14. The other end of the operation wire 11 is mounted to a guide part 18 which is fitted in the elongate groove 14.

With the above structure, when a treatment is performed in a body cavity, the instrument main body 1 is thermally disinfected by thermal sterilization before it is used. When the instrument main body 1 is thermally disinfected, the crystal structure of the shape memory alloy of the disinfection indicator 17 is reversely modified from the martensite phase to the mother phase. Therefore, independently of the shape due to plastic deformation of the deformable portion 17a before the disinfection indicator 17 is heated, the disinfection indicator is restored to a linear shape, as shown in FIG. 1. Since the disinfection indicator 17 comprises the shape memory alloy which has the one-way shape memory effect, the disinfection indicator will not be deformed even if the mother phase of the crystal structure is modified to the martensite phase. Thus, once the medical instrument is thermally disinfected, the deformable portion 17a of the disinfection indicator 17 is changed from its initial curved shape to a linear shape, thus allowing easy visual checking of disinfection of the medical instrument.

When a finger is inserted in the finger insertion part 16 of the instrument main body 1 which is in use and when the slider 13 is being slid, the push bar 10 is reciprocally moved through the operation wire 11. In synchronism with the reciprocal movement of the push bar 10, the treatment members 7 are opened and closed through the arms 9. When the slider 13 is pulled and slid toward the finger insertion part 16 so as to close the treatment members 7, the user's finger exerts an external force which acts on the deformable portion 17a of the disinfection indicator 17 and the deformable portion 17a is plastically deformed into a curved shape, as shown in FIG. 2. The medical instrument which is used once is easily checked by the curved shape of the disinfection indicator 17.

With the above structure, the indicating means for indicating whether the medical instrument has been used is provided only with the disinfection indicator 17 at the finger insertion part 16 of the instrument main body 1. Therefore, assembly of the disinfection indicator 17 may be simplified. Therefore, the disinfection indicator 17 according to the present invention is of a simple structure. The disinfection indicator 17 can be mounted in a relatively small space.

Figure 3:
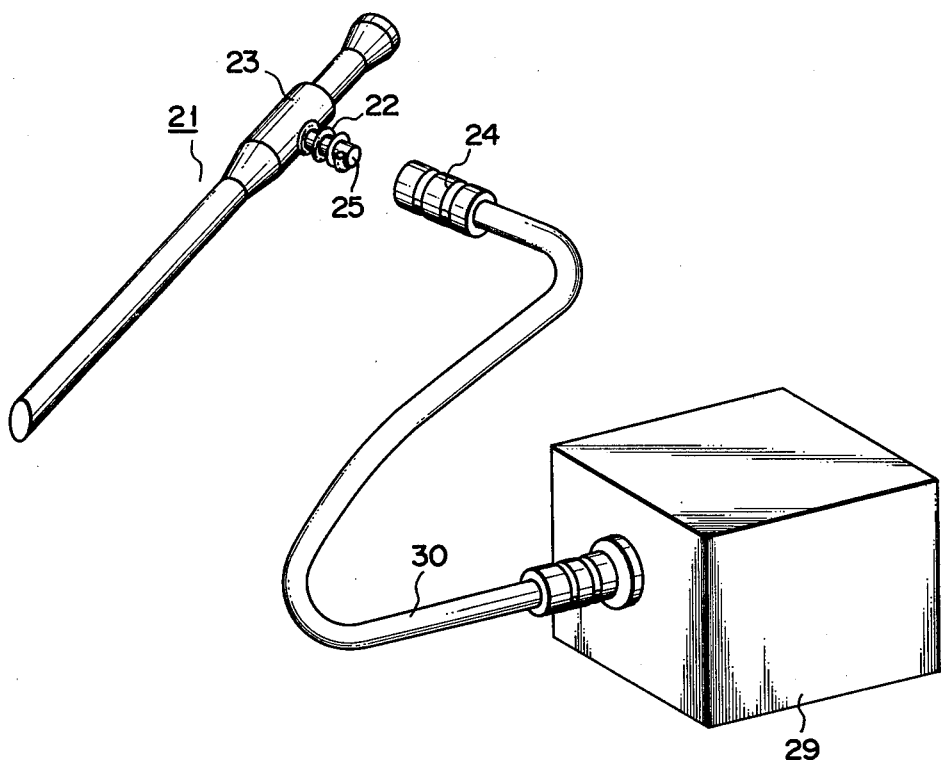
Figure 4:
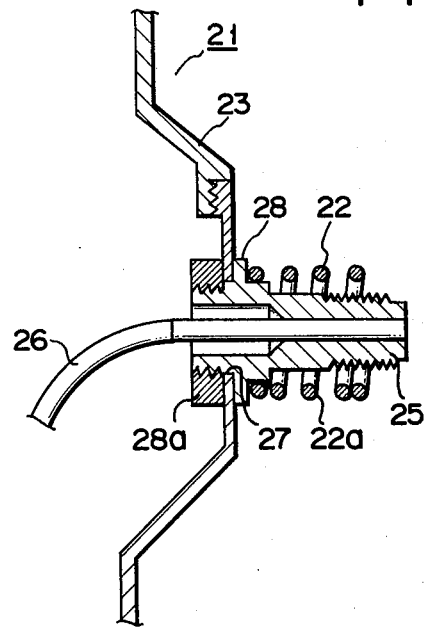
Figure 5:
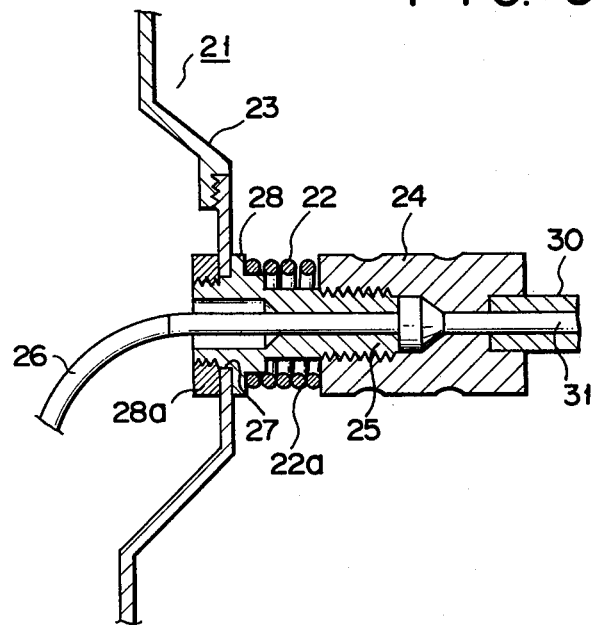

A disinfection indicator according to a second embodiment of the present invention will be described with reference to FIGS. 3 to 5. A disinfection indicator 22 is mounted to a main body 21 of a rigid tube type endoscope. A connector plug 25 which is detachable from a connector 24 to be described later extends from a grip 23 of the main body 21. A hole in which a light guide 26 is fitted is formed in the connector plug 25, as shown in FIGS. 4 and 5. One end of the light guide 26 is exposed to the outside. The base of the connector plug 25 is inserted from the outside into a mounting hole 27 formed in the side wall of the grip 23. A flange 28 of the connector plug 25 is pushed toward the grip 23 and the connector plug 25 is fixed at the inside of the grip 23 with a fixing ring 28a. The disinfection indicator 22 is coaxial with the outer circumference of the connector plug 25. The disinfection indicator 22 has a deformable portion 22a of a coil shape. The base of the deformable portion 22a is mounted to the flange 28 of the connector plug 25. When the disinfection indicator 22 is heated to a temperature of 50° to 100° C. or higher by thermal sterilization, the parent phase (high temperature phase) of the crystal structure of the shape memory alloy is established and the coil of the deformable portion 22a expands, as shown in FIG. 4, since the disinfection indicator 22 is made of the shape memory alloy of the one-way shape memory effect. Thus, the expanding shape of the coil of the disinfection indicator 22 indicates disinfection of the main body 21. The connector 24 is connected to a light source device 29 through a flexible tube 30. A light guide 31 is disposed inside the flexible tube 30. The top of the light guide 31 is fitted on the connector 24. When the connector 24 is screwed to the connector plug 25, the disinfection indicator 22 is pushed by the front surface of the connector 24 upon movement of the connector 24 from the top of the connector plug 25 to the base thereof. As shown in FIG. 5, when the connector 24 which is screwed onto the connector plug 25 is mounted at the normal spiral position, the coil of the deformable portion 22a of the disinfection indicator 22 is compressed and plastically deformed to be a contracted shape. Further, in a condition in which the connector 24 is screwed onto the connector plug 25 to the normal position, the front surface of the light guide 31 on the side of the light source device 29 opposes one end face of the light guide 26 on the side of the endoscope. Light emitted from the light source device 29 is guided to the light guide 26 through the light guide 31.

With the above structure, the main body 21 of the rigid tube type endoscope is thermally disinfected as the connector 24 is removed from the connector plug 25. When the main body 21 is heated for thermal sterilization, the crystal structure of the shape memory alloy of the disinfection indicator 22 is reversely modified from the martensite phase to the mother phase. Therefore, the deformable portion 22a of the disinfection indicator 22 is restored to the expanding shape, as shown in FIG. 4. Further, since the disinfection indicator 22 is made of the shape memory alloy with the one-way shape memory effect, the alloy is not deformed when the crystal structure is modified from the mother phase to the martensite phase. Therefore, when the rigid tube type endoscope is thermally disinfected once, disinfection is easily checked by the shape of the deformable portion 22a of the disinfection indicator 22. On the other hand, when the rigid tube type endoscope is used, the coil of the deformable portion 22a of the disinfection indicator 22 is contracted. Thus, the used medical equipment is easily and visually checked. With the above structure, the same effect as in the first embodiment is obtained.

Figure 6:
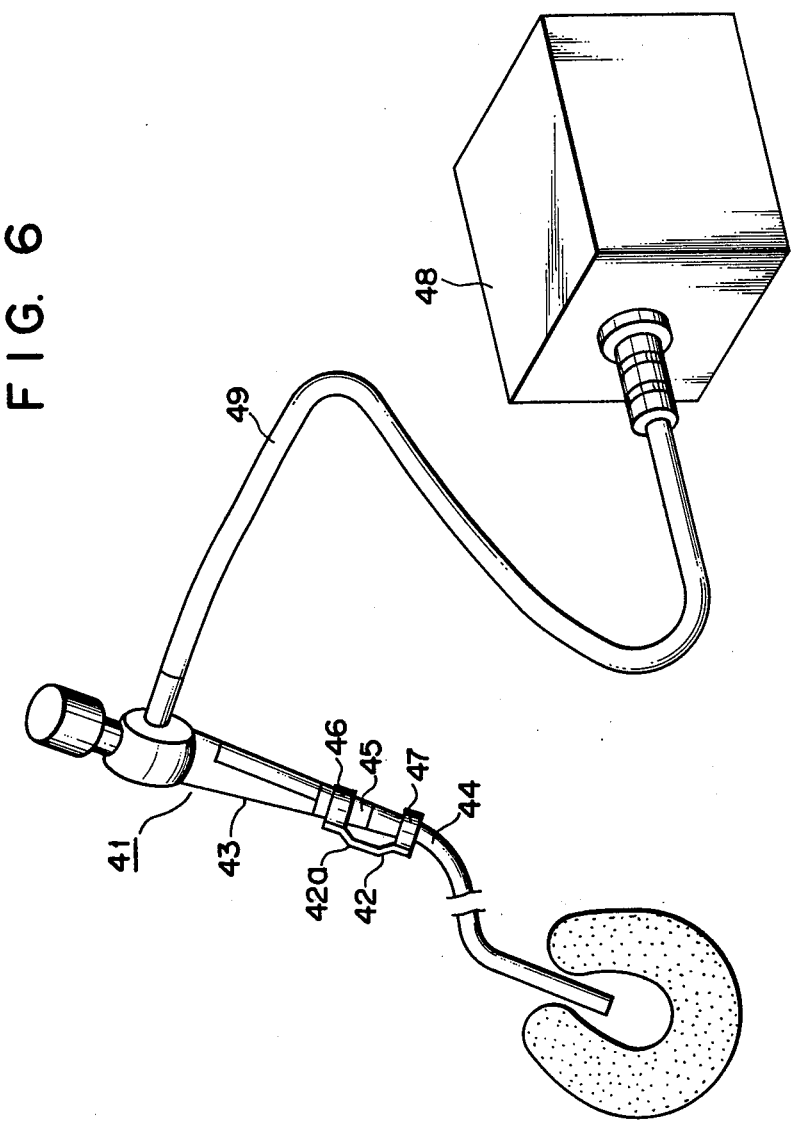
Figure 7:
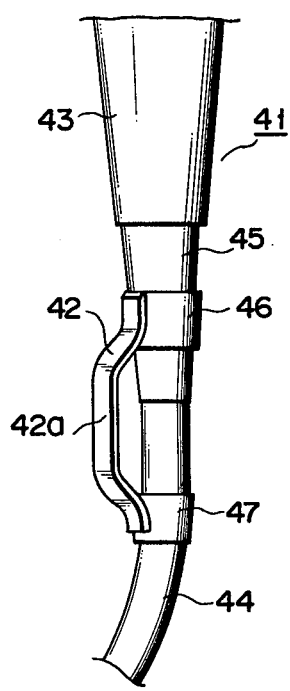
Figure 8:
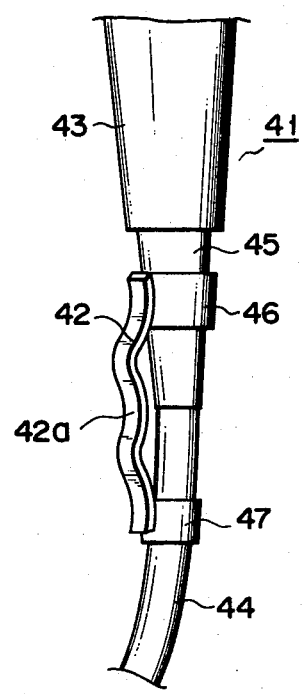

A disinfection indicator according to a third embodiment of the present invention will be described with reference to FIGS. 6 to 8. A disinfection indicator 42 is mounted to a main body 41 of a flexible tube type endoscope (medical equipment). A non-bending part 45 is formed between an operation part 43 and an insertion part 44 of the main body 41. Support rings 46 and 47 are detachably mounted to the non-bending part 45 and the insertion part 44, respectively. The disinfection indicator 42 is hooked across the support rings 46 and 47. The disinfection indicator 42 is of a plate shape. One end of the disinfection indicator 42 is mounted on the support ring 47 and the other end thereof is mounted to the support ring 46 on the side of the non-bending part 45. Further, a portion between both ends of the disinfection indicator 42 is defined as a deformable part 42a. When the disinfection indicator 42 is heated to a temperature of 50° to 100° C. or higher for thermal sterilization, the deformable part 42a becomes a smooth arcuated shape in the mother phase (high temperature phase) of the crystal structure of the shape memory alloy, as shown in FIG. 7, since the disinfection indicator 42 is made of the shape memory alloy having the one-way shape memory effect. The smooth arcuated shape indicates disinfection of the medical equipment. Reference numeral 48 denotes a light source device, and reference numeral 49 denotes a flexible tube which stores a light guide for guiding light emitted by the light source device 48 into the main body 41.

With the above structure, when the main body 41 of the flexible tube type endoscope is thermally disinfected, the deformable part 42a of the disinfection indicator 42 is restored to a smooth arcuated shape which indicates disinfection of the endoscope, as shown in FIG. 7. Thereafter, when a hand grasps the operation part 43 of the endoscope which is in use the force acts on the deformable portion 42a of the disinfection indicator 42, as shown in FIG. 8, and the deformable portion 42a is deformed into a corrugated shape. Disinfection of the medical equipment can be visually checked by the shape of the deformable portion 42a of the disinfection indicator 42. In other words, it can be judged whether or not the main body 41 of the flexible tube type endoscope has been disinfected by thermal sterilization.

With the above structure, the same effects as in the first and second embodiments are obtained.

A disinfection indicator according to a fourth embodiment will be described with reference to FIGS. 9 and 10. FIGS. 9 and 10 show a treatment instrument (medical equipment) for an endoscope which is to be inserted into a channel for forceps of the endoscope, in the same manner as in the first embodiment. The same reference numerals as in FIGS. 9 and 10 denote the same parts in FIGS. 1 and 2, and a detailed description thereof will be omitted. A hole 51 is formed in the finger insertion part 16 to communicate with the finger insertion hole 15 and a disinfection indicator 52 is disposed in the hole 51. The disinfection indicator 52 comprises a columnar indication member 54 which has a flange 53 and an operation member (deformable portion) 55 of a V shape. The indication member 54 is free to move reciprocally in the hole 51 and may be completely inserted inside the hole 51 to the finger insertion hole 15. One end of the operation member 55 is firmly mounted to the inner bottom of the hole 51 and the other end thereof is firmly mounted to the indication member 54. Since the operation member 55 is made of the shape memory alloy having the one-way shape memory effect, when the operation member 55 is heated to a temperature of 50° to 100° C. or higher for thermal sterilization, the one-way shape memory is effected. When the crystal structure of the shape memory alloy of the operation member 55 is kept in the mother phase (high temperature phase), the operation member 55 is kept in a V shape, as shown in FIG. 9. At this time, the indication member 54 extends from the hole 51 into the finger insertion hole 15. Thus, disinfection is indicated by the extended position of the indication member 54.

With the above structure, when the main body 1 is thermally disinfected, the operation member 55 is restored to the shape which indicates disinfection of the medical equipment, as shown in FIG. 9. The indication member 54 is now in the extending position. However, when a finger is inserted into the finger insertion part 16 of the endoscope which is in use, the force acts on the indication member 54 and the indication member 54 is pushed inside the hole 51. Therefore, the operation member 55 is plastically deformed to a closed V shape, as shown in FIG. 10. The indication member 54 is thus housed inside the hole 51. It is, therefore, easily and visually judged whether the main body 1 has been thermally disinfected by the position of the indication member 54.

Figure 11:
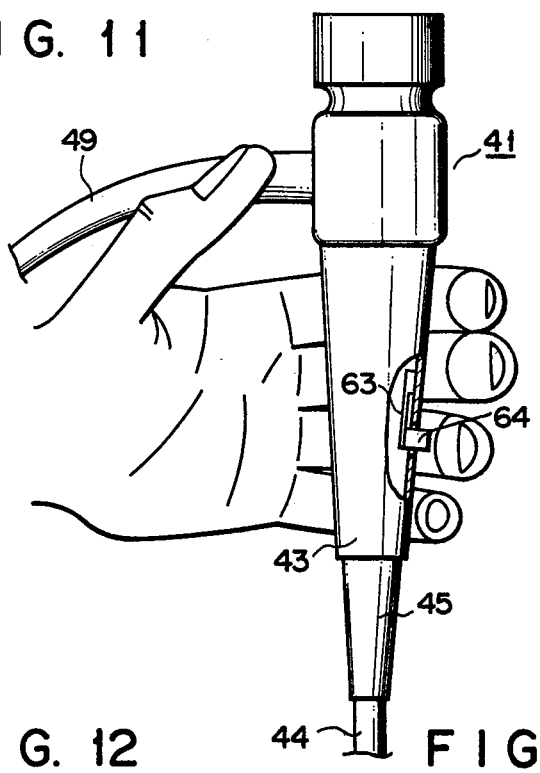
Figure 12:
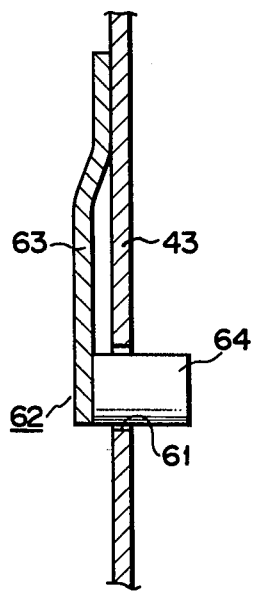
Figure 13:
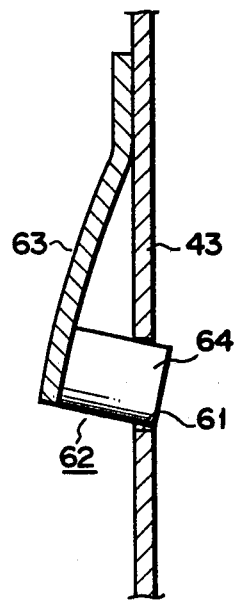

A disinfection indicator according to a fifth embodiment of the present invention will be described with reference to FIGS. 11 to 13. FIGS. 11 to 13 show the same flexible tube type endoscope (medical equipment) as in the third embodiment of FIGS. 6 to 8. The same reference numerals as in FIGS. 11 to 13 denote the same parts in FIGS. 6 to 8, and a detailed description thereof will be omitted. Further, in the fifth embodiment, a through hole 61 is formed in the side wall of the operation part 43 and a disinfection indicator 62 is disposed on the operation part 43. The disinfection indicator 62 includes an operation member (deformable portion) 63 of a plate shape the end of which is fixed to the inner surface of the side wall of the operation part 43, and an indication member 64 which is mounted to the other end of the operation member 63 and which extends to the outside through the through hole 61. The operation member 63 is made of the shape memory alloy which shows the one-way shape memory effect when it is heated to a temperature of 50° to 100° C. or higher for thermal sterilization. The operation member 63 is made of the shape memory alloy the crystal structure of which is kept in the mother phase (high temperature phase) so as to establish linearity of the operation member 63, as shown in FIG. 12. When the operation member 63 is substantially linear, the indication member 64 is kept in the extending position in which the indication member 64 extends through the through hole 61. Thus, disinfection of the medical equipment can be visually checked. In other words, it can be visually judged that the main body 41 is thermally disinfected. However, when the endoscope is in use, the user holds the operation part 43 and the indication member 64 is pushed into the through hole 61, as shown in FIG. 13. In response to this, the operation member 63 is plastically deformed. Therefore, if it is judged that the indication member 64 is kept at the extended position, it is easily and visually judged that the main body 41 has been thermally disinfected.

Figure 14:
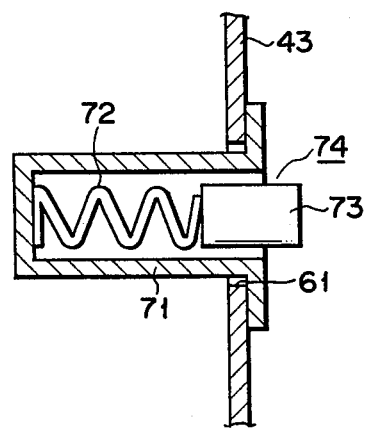
Figure 15:
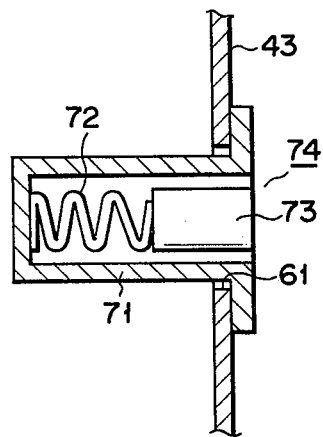

The present invention is not limited to the above embodiments. For example, as shown in a sixth embodiment of FIGS. 14 and 15, a housing member 71 of a cylindrical shape with a bottom is mounted from the inside of the through hole 61 of the operation part 43 of the fifth embodiment. A disinfection indicator 74 may include an operation member (deformable portion) 72 the end of which is mounted to the inner bottom surface of the housing member 71 and which is housed in the housing member 71, and an indication member 73 which is mounted to the other end of the operation member 72. The operation member 72 is made of a shape memory alloy which provides a one-way shape memory effect when the operation member 72 is heated to a temperature of 50° to 100° C. or higher for thermal sterilization. When the crystal structure of the shape memory alloy is in the mother phase (high temperature phase), the coil has the extending shape, as shown in FIG. 14. When the coil of the operation member 72 is kept in the expanding shape, the indication member 73 extends from the housing member 71, as shown in FIG. 14. Disinfection is indicated by the shape. In particular, disinfection of the medical equipment can be visually checked. However, when the main body 41 is used, the indication member 73 is pushed into the housing member 71, as shown in FIG. 15, and the coil of the operation member 72 is compressed. It can be visually judged that the medical instrument has been used.

The disinfection indicator 17 of the first embodiment of FIGS. 1 and 2 may have a structure wherein one end of the disinfection indicator 17 is mounted to the finger insertion part 16 and the other end thereof is a free end.

Further, the operation member 55 according to the fourth embodiment of FIGS. 9 and 10 may have a W shape by bending a plate material a plurality of times. Alternatively, the indication member 54 may be integrally formed with the operation member 55.

Further, the disinfection indicator may be made of a shape memory alloy and a deformable portion thereof may be deformed at a temperature of 100° to 120° C. in the mother phase. Further, a plurality of disinfection indicators may have deformable portions and the reverse modification temperatures of the deformable portions may be respectively different. These disinfection indicators may be mounted on a single medical instrument. With this arrangement, the disinfection temperature may be checked properly. Further, the disinfection indicator may be mounted on various pieces of medical equipment such as surgical knives, surgical forceps, band pieces of laser surgical knives, instruments for assisting insertion of an endoscope and medical equipment storage containers, which are repeatedly used after thermal sterilization.

Figure 16:
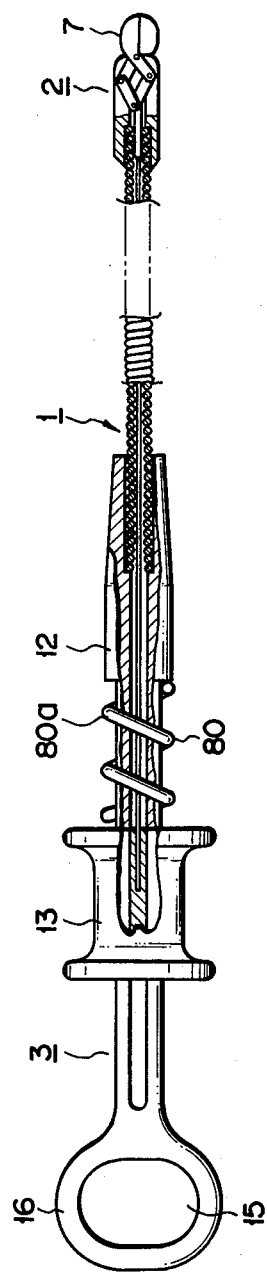
Figure 17:
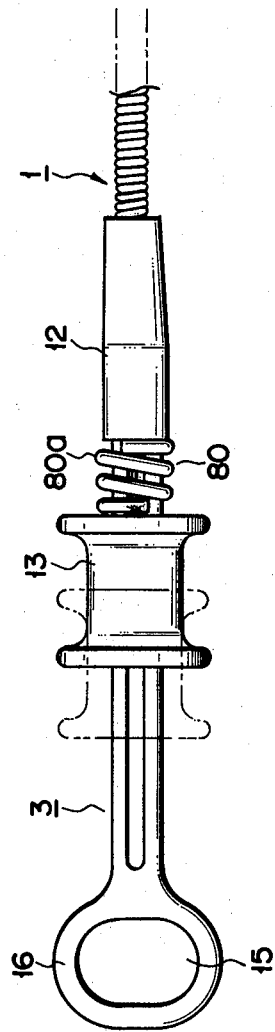

A disinfection indicator according to a seventh embodiment of the present invention will be described with reference to FIGS. 16 and 17. FIGS. 16 and 17 show a biopsy forceps (a medical instrument for an endoscope) in the same manner as in the first embodiment. The same reference numerals as in FIGS. 16 and 17 denote the same parts in FIGS. 1 and 2, and a detailed description thereof will be omitted. A disinfection indicator 80 of a coil shape is disposed in a moving path of the slider 13 on the operation main body 12. The disinfection indicator 80 has a deformable portion 80a of a coil shape. The deformable portion 80a is made of the shape memory alloy which has the one-way shape memory effect when the operation main body 12 is heated to a temperature of 50° to 100° C. or higher. When the crystal structure of the shape memory alloy is in the mother phase (high temperature phase), the coil of the deformable portion 80a has an extended shape, as shown in FIG. 16. The extended shape indicates disinfection of the biopsy forceps.

With the above structure, when the main body 1 is thermally disinfected, the coil of the deformable portion 80a of the disinfection indicator 80 is deformed to the extended shape, as shown in FIG. 16. When the main body 1 is to be used, the slider 13 is separated from the finger insertion part 16 so as to open the treatment members 7. In response to the movement of the slider 13, the disinfection indicator 80 is pressed by the slider 13, as indicated by the solid line of FIG. 17. Thus, the coil is compressed and deformed plastically. It can be visually easily judged whether the main body has been thermally disinfected by checking the shape of the disinfection indicator 80. Therefore, the assembling operation is simplified. Further, the disinfection indicator of this type can be mounted in a relatively small space.

Figure 18:
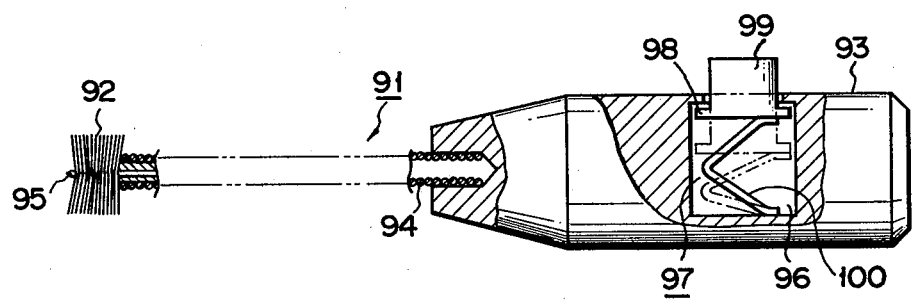
FIG. 18 is a partially cutaway side view of a disinfection ihdicator of medical equipment according to an eighth embodiment of the present invention.

A disinfection indicator according to an eighth embodiment of the present invention will be described with reference to FIG. 18. Referring to FIG. 18, reference numeral 91 denotes a main body of a cytodiagnostic brush (instrument for the endoscope). A brush (treatment part 92) is formed at the top of the main body 91 and an operation part 93 of a columnar shape is formed at the base of the main body 91. The base of an insertion member 94 consisting of a flexible tube is mounted on one end of the operation part 93. A wire 95 is mounted at the top of the insertion member 94. Part of the wire 95 extends from the top of the insertion member 94. The brush 92 is attached to the extended portion of the wire 95. Further, a hole 96 opening to the outer circumference of the operation part 93 is formed. A disinfection indicator 97 is disposed inside the hole 96. The disinfection indicator 97 comprises a columnar indication member 99 which has a flange 98 and an operation member (deformable portion) 100 of a V shape. The indication member 99 is free to move within the hole 96. The operation part 93 is free to project or recess from the outer circumferential surface. One end of the operation member 100 is mounted to the inner bottom of the hole 96. The other end of the operation member 100 is mounted to the indication member 99. The operation member 100 is made of the shape memory alloy which provides the one-way shape memory effect when the operation member 100 is heated to a temperature of 50° to 100° C. or higher for thermal sterilization. When the crystal structure of the shape memory alloy is in the mother phase (high temperature phase), the operation member 100 is kept in an open V shape as indicated by the solid line of FIG. 18. At this time, the indication member 99 extends from the hole 96, thus indicating disinfection of the cytodiagnostic brush.

With the above structure, when the main body 91 is thermally disinfected, the operation member 100 is restored to the shape which indicates disinfection of the medical instrument as indicated by the solid line of FIG. 18. The indication member 99 is kept in the extending position. However, when this medical instrument is in use, and when the operation part 93 is grasped, force is acted on the indication member 99 which is pushed into the hole 96 by the finger and the operation member 100 is plastically deformed into a closed V shape as indicated by the alternate long and two dashed lines. Therefore, it can be easily judged whether the main body 91 has been thermally disinfected by visually checking whether or not the indication member 99 is positioned in the extended position.

Figure 19:
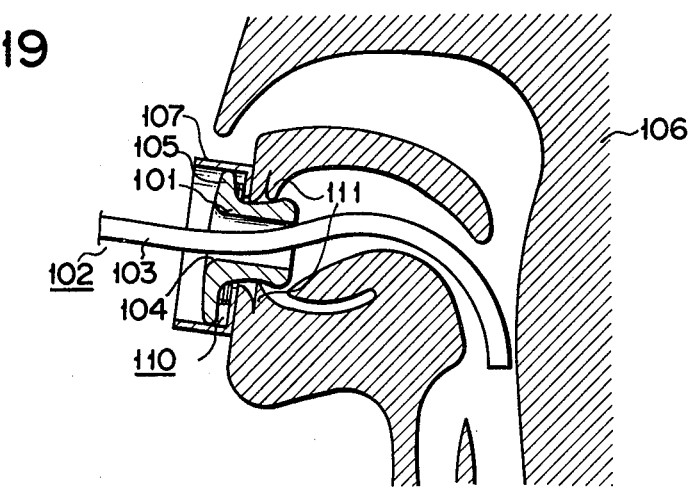
Figure 20:
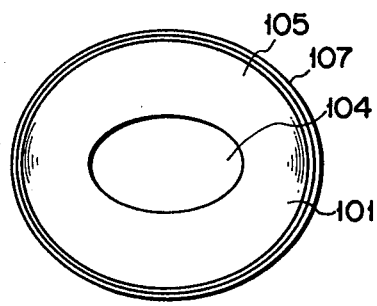
Figure 21:
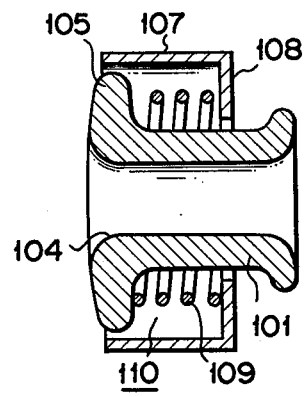

A disinfection indicator according to a ninth embodiment of the present invention will be described with reference to FIGS. 19 to 21. Reference numeral 101 denotes a main body of a mouthpiece (instrument for assisting insertion of the endoscope). The main body 101 is substantially of a cylindrical shape. An endoscope insertion hole 104 the diameter of which is sufficiently larger than the outer diameter of an insertion part 103 of an endoscope 102 is formed inside the mouthpiece 101. A projection 105 which extends in the radial direction thereof is formed at one end (left side in FIGS. 19 and 21) of the main body 101. The other end of the main body 101 is an insertion end which is inserted into a mouth of a patient 106. Reference numeral 107 denotes an outer ring which has a projection 108 extending inside toward the insertion end and the section of which has an L shape. The outer ring 107 is free to move reciprocally along the outer circumferential surface of the main body 101. An operation part (deformable portion) 109 of a coil shape is disposed between the outer ring 107 and the main body 101. One end of the operation member 109 is mounted to the projection 108 of the outer ring 107 and the other end thereof is mounted to the projection 105 of the main body 101. The operation member 109 is made of the shape memory alloy in the same manner as in the previous embodiments. A disinfection indicator 110 comprises the operation member 109 and the outer ring 107. When the crystal structure of the shape memory alloy is in the mother phase (high temperature phase), the coil of the operation member 109 expands, as shown in FIG. 21. In this condition, the outer ring 107 is kept inwardly of the projection 105 of the main body 101. This position indicates disinfection of the mouthpiece.

With the above structure, the mouthpiece is thermally disinfected by thermal sterilization. When the main body 101 is thermally disinfected, the crystal structure of the shape memory alloy of the operation member 109 is reversely modified from the martensite phase to the mother phase. Even if the operation member 109 is plastically deformed before heating, the extended shape of the coil of the operation member 109 is restored, as shown in FIG. 21. Further, since the operation member 109 is made of the shape memory alloy having the one-way shape memory effect, the operation member 109 will not be modified when the crystal structure is changed from the mother phase to the martensite phase. Once the main body 101 is thermally disinfected by thermal sterilization, the outer ring 107 is kept inwardly of the projection 105 of the main body 101, thus visually indicating disinfection of the mouthpiece.

When the mouthpiece is used, the insertion end is inserted into the mouth of the patient 106 and the mouthpiece is held between upper and lower teeth 111. In this condition, the insertion part 103 of the endoscope 102 is inserted through the endoscope insertion hole 104 and further into a predetermined body cavity. When the main body 101 is held by the upper and lower teeth 111 as shown in FIG. 19, the outer ring 107 is pushed toward the projection 105 of the main body and the coil of the operation member 109 is compressed and plastically deformed. Once the main body 101 is used, the outer ring 107 is pushed beyond the projection 105 of the main body 101, thus indicating that the mouthpiece has been used and is not sterile.

The construction of the disinfection indicator 110 is simplified. Further, the disinfection indicator 110 requires only a relatively small space and assembly thereof is very easy.

Figure 22:
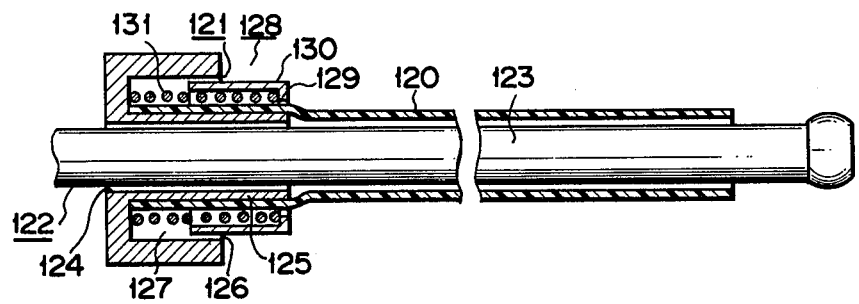
Figure 23:
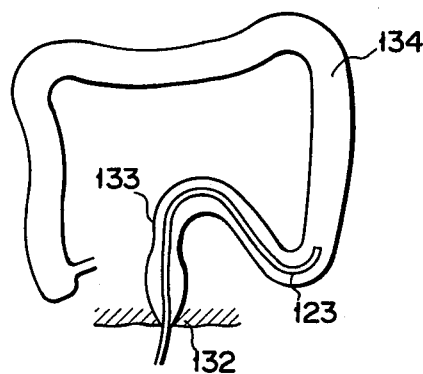
Figure 24:
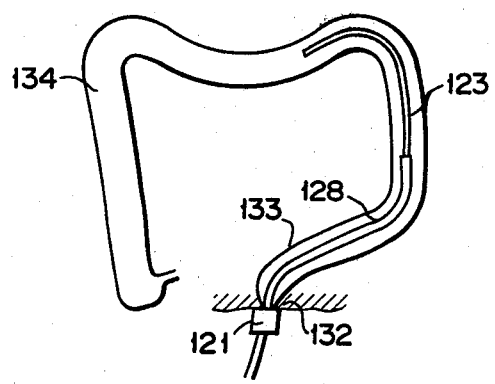

A disinfection indicator according to a tenth embodiment of the present invention will be described with reference to FIGS. 22 to 24. Referring to the figure, reference numeral 121 denotes a main body of an endoscope insertion assisting instrument. A tubular part 125 having an endoscope insertion hole 124 the diameter of which is sufficiently larger than the outer diameter of an insertion part 123 of an endoscope 122 is formed in the main body 121. A ring-shaped housing recess 127 which communicates with a ring-shaped opening 126 is formed in the end face at the side (left side in FIG. 22) of the insertion end of the main body 121. A flexible tube 120 is fitted in the tubular part 125. A disinfection indicator 128 is disposed in the housing recess 127. The disinfection indicator 128 comprises a tubular indication member 130 which has an extended part 129 extending toward the inside, and an operation member (deformable portion) 131 of a coil shape. The indication member 130 is free to move reciprocally in the housing recess 127 and is free to project into the housing recess 127 and to disappear thereinto. One end of the operation member 131 is mounted on the inner bottom surface of the housing recess 127 and the other end thereof is mounted to the indication member 130. The operation member 131 comprises the shape memory alloy which shows the one-way shape memory effect when the operation member 131 is heated to a temperature of 50° to 100° C. or higher for thermal sterilization. When the crystal structure of the shape memory alloy is in the mother phase (high temperature phase), the coil of the operation member 131 extends as shown in FIG. 22. In this condition, the indication member 130 extends from the housing recess 126 and is kept at the extending position, thus visually indicating disinfection of the endoscope insertion assisting instrument.

With the above structure, when the main body 121 is thermally disinfected, the operation member 131 is restored to a shape which indicates disinfection of the assisting instrument, as shown in FIG. 22. Since the indication member 130 is kept in the extending position, disinfection of the auxiliary instrument can be visually checked. When this auxiliary instrument is in use, the insertion part 123 of the endoscope 122 is inserted in the endoscope insertion hole 124 of the main body 121 in advance. The insertion part 123 is inserted through an anus 132 to a large intestine 134 through a colon 133 of an S shape of the patient. In this case, when the top of the insertion part 123 passes through the colon 133 of the S shape as shown in FIG. 23, the top of the insertion part 123 is curved so as to hang on the colon 133 of the S shape. The insertion part 123 is pulled so as to substantially straighten the S-shape colon 133. Thereafter, the flexible tube 120 is inserted into the colon 133 which is kept substantially straight, as shown in FIG. 24. Therefore, the insertion part 123 can be inserted to a desired position. When the flexible tube 120 is inserted in the colon 133, the indication member 130 is pushed into the anus 132. The indication member 130 is pushed into the housing recess 127 and the coil of the operation member 131 is compressed and deformed plastically. When the main body 121 is used once, the indication member 130 is housed in the housing recess 127, thus visually indicating that the auxiliary instrument has been used.

Figure 25:
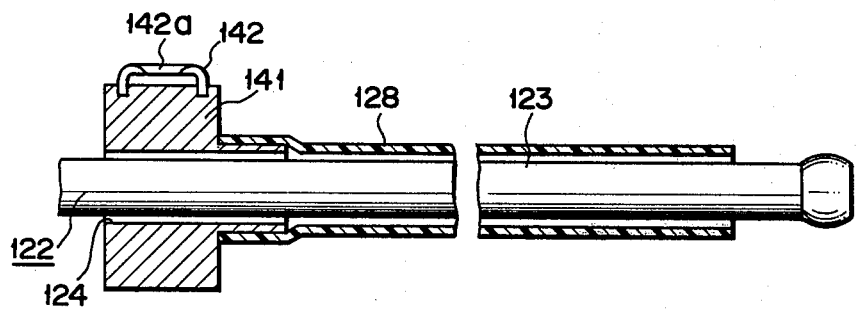
FIG. 25 is a sectional view of a disinfection indicator of a modification of the tenth embodiment of FIG. 22.

In a modification of an endoscope insertion assisting instrument of FIG. 25, a disinfection indicator 142 which has a deformable part 142a of a rod shape is disposed on the outer circumference of a main body 141. The disinfection indicator 142 is made of the shape memory alloy which shows the one-way shape memory effect when the disinfection indicator 142 is heated to a temperature of 50° to 100° C. or higher. When the crystal structure of the shape memory alloy is in the mother phase (high temperature phase), the deformable portion 142a is kept substantially in the linear shape which indicates disinfection of the endoscope insertion assisting instrument, as indicated by the solid line of FIG. 25. When the main body 141 is used, the deformable portion 142a is pressed by the anus of the patient and deformed to a curved shape, thus visually indicating that the auxiliary instrument has already been used.

Further, the disinfection indicator may comprise a shape memory alloy which shows a one-way shape memory effect when the disinfection indicator is heated to a temperature of 100° to 120° C. A plurality of disinfection indicators which are reversely modified to the mother phase at different temperatures may be mounted on a single endoscope. In this case, the disinfection temperature is checked accurately. Endoscope insertion assisting instruments may include flexible endotracheal tubes and tracheal tubes for a rigid tube type endoscopes as well.

Figure 26:
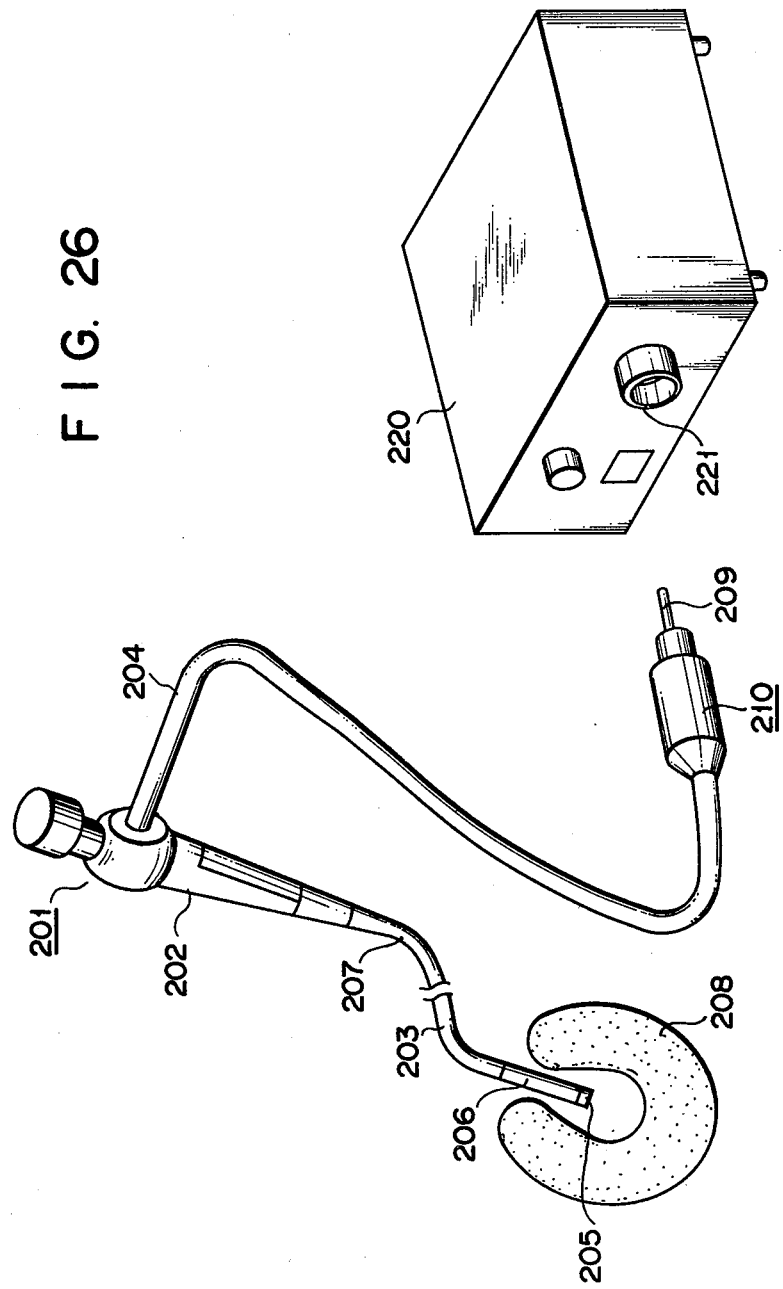
Figure 27:
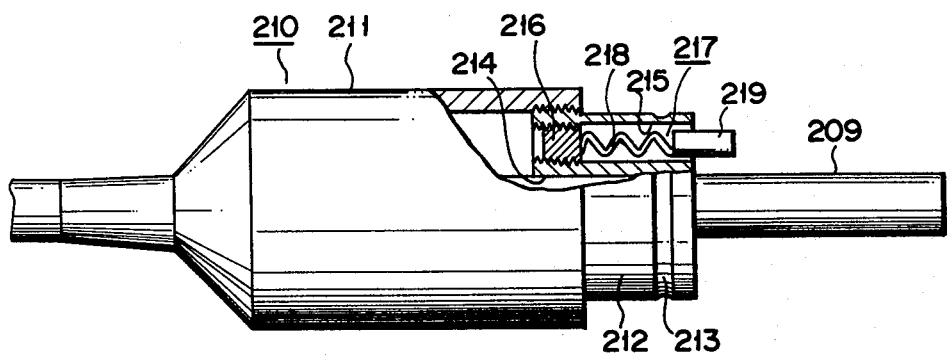
Figure 28:
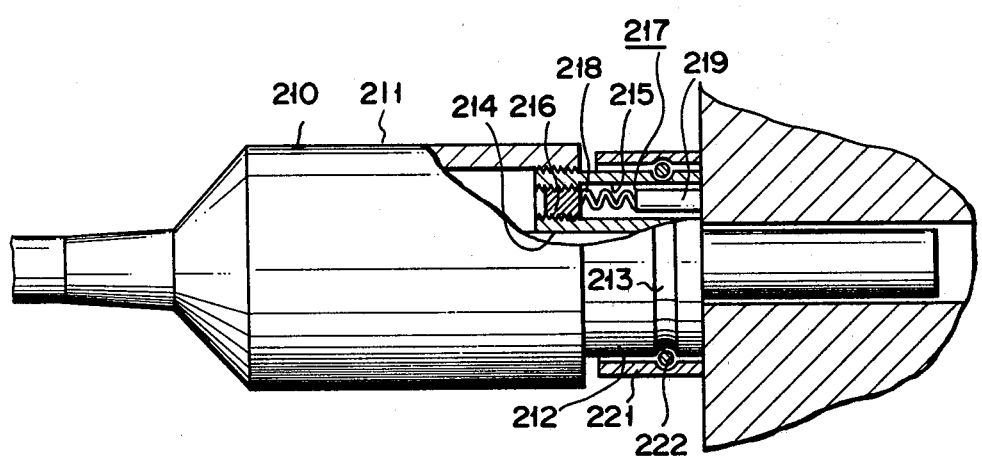

A disinfection indicator according to an eleventh embodiment of the present invention will be described with reference to FIGS. 26 to 28. Reference numeral 201 denotes a main body of the flexible tube type endoscope. The main body 201 comprises an operation part 202, an insertion part 203 and a light guide cable 204. The insertion part 203 includes a top portion 205, a flexible portion 206 and a connecting portion 207. The flexible portion 206 is bent in response to an operation by the operation part 202 and the top portion 205 is guided into a body cavity 208. A light guide 209 is housed in the light guide cable 204. A connector 210 is mounted on the top of the light guide 209. The connector 210 comprises a cylindrical connector main body 211 with an open top, and a small-diameter insertion body 212 which is screwed in the open end of the connector main body 211, as shown in FIGS. 27 and 28. A stop groove 213 of a ring shape is formed on the outer circumferential surface of the insertion body 212. A fitting hole 214 is fitted around the light guide 209 inside the insertion body 212. At the same time, the top of the light guide 209 extends to the outside. Further, a circular hole 215 which is parallel to the fitting hole 214 is formed. A holding member 216 is disposed at the base (end toward the side of the connector main body 211) of the circular hole 215. A disinfection indicator 217 is mounted on the holding member 216. The disinfection indicator 217 comprises a coil-shaped operation member (deformable portion) 218 one end of which is connected to the holding member 216 and a columnar indication member 219 which is mounted to the other end of the operation member 218. The indication member 219 is made of the shape memory alloy which shows the one-way shape memory effect. When the crystal structure of the shape memory alloy of the operation member 218 is in the mother phase (high temperature phase), the coil of the operation member 218 is expanded, as shown in FIG. 27. In this condition, the indication member 219 extends from the circular hole 215 and is kept in this extending position, thus indicating disinfection of the endoscope. The connector 210 of the above arrangement is connected to a light source unit 220. A connector plug 221 of a cylindrical shape is disposed at the light source unit 220. A positioning ring 222 is disposed on the inner circumferential surface of the connector plug 221. The insertion body 212 of the connector 210 is inserted into the connector plug 221. When the insertion body 212 is inserted to the normal mounting position, as shown in FIG. 28, the positioning ring 222 is fitted in the stop groove 213 of the insertion body 212. Thus, inadvertent removal of the insertion body 212 from the connector plug 221 is prevented properly.

When the endoscope of the above structure is to be used for examining the body cavity and providing a treatment, the main body 210 is thermally disinfected by thermal sterilization. When the main body 210 is thermally disinfected, the crystal structure of the shape memory alloy of the operation member 218 is modified from the martensite phase to the mother phase. Therefore, independently of the phase of the operation member 218 before heating, the coil of the operation member 218 expands, as shown in FIG. 27. Further, since the operation member 218 is made of the shape memory alloy which shows the one-way shape memory effect when the operation member 218 is heated, the operation member 218 will not be deformed when the crystal structure is modified from the mother phase to the martensite phase. Once the flexible tube type endoscope is thermally disinfected, the indication member 219 is extended from the circular hole 215, thus visually indicating disinfection of the endoscope.

When this endoscope is in use, the insertion body 212 of the connector 210 is inserted into the connector plug 221. Further, when the insertion body 212 is inserted to the normal mounting position within the connector plug 221, the indication member 219 presses on the inner bottom surface of the connector plug 221 and the operation member 218 is compressed. When the insertion body 212 is inserted to the normal mounting position, the indication member 219 is pushed into the circular hole 215 and the coil of the operation member 218 is compressed and deformed plastically. Therefore, once the endoscope is used, the indication member 219 is pushed into the circular hole 215, thus visually indicating that the endoscope has been used and is no longer sterile.

Figure 29:
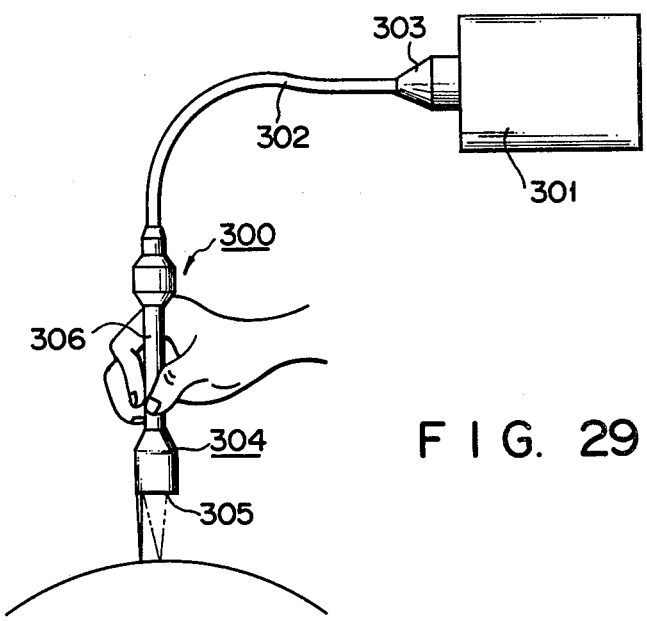
Figure 30:
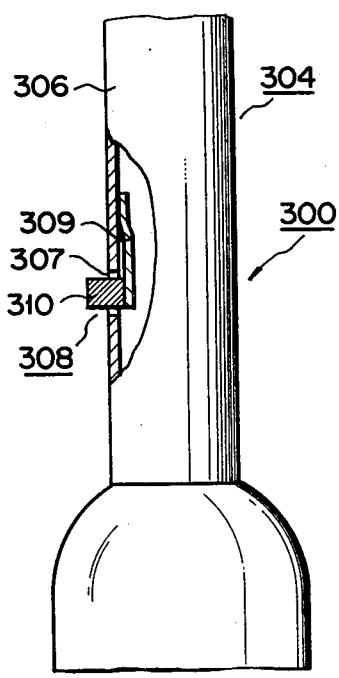

A disinfection indicator according to a twelfth embodiment of the present invention will be described with reference to FIGS. 29 to 31. Reference numeral 301 denotes a laser which emits laser beams. One end of a flexible tube 302 which houses a laser guide (not shown) is detachably connected to the laser 301 through a connector 303. The other end of the flexible tube 302 is mounted to a handpiece 304. The laser beam emitted from the laser 301 is guided to the handpiece 304 through the laser guide within the flexible tube 302. The laser beam is radiated to the outside from a radiation end face 305 of the handpiece 304. The flexible tube 302 and the handpiece 304 are defined as a part 300 to be thermally disinfected before they are used. A through hole 307 is formed in a cylindrical body 306 of the handpiece 304. At the same time, a disinfection indicator 308 which is free to appear or disappear through the through hole 307 is provided. The disinfection indicator 308 comprises a plate-shaped operation member 309 one end of which is mounted to the inner wall surface of the cylindrical body 306 and an indication member 310 which is mounted to the other end of the operation member 309. This indication member 310 is inserted into the cylindrical body 306 and extends from the cylindrical body 306 through the through hole 307. The operation member 309 is made of the shape memory alloy which shows the one-way shape memory effect. When the crystal structure of the shape memory alloy is in the mother phase (high temperature phase), the operation member 309 is kept in a linear shape, as shown in FIG. 30. In this condition, the indication member 310 extends through the through hole 307 and is kept in the extended position, thus visually indicating disinfection of the laser instruments. Thus, it can be easily and visually checked whether the part 300 has been thermally disinfected.

When laser therapy is to be performed with the laser of the above structure, the part to be disinfected such as the flexible tube 302 and the handpiece 304 is disinfected by thermal sterilization. When the part 300 is thermally disinfected, the crystal structure of the shape memory alloy of the operation member 309 is modified from the martensite phase to the mother phase. Therefore, even if the operation member 309 is deformed plastically in a curved shape before heating, the operation member 309 is restored to the linear shape, as shown in FIG. 30. The indication member 310 extends through the through hole 307, thus indicating disinfection of the medical instrument. Further, since the operation member 309 is made of the shape memory alloy which shows the one-way shape memory effect when it is heated, the indication member 310 will not be deformed when the crystal structure thereof is modified from the mother phase to the martensite phase. Once the part 300 to be disinfected is thermally disinfected, the indication member 310 extends through the through hole 307, thus visually indicating disinfection of the medical instrument.

Figure 31:
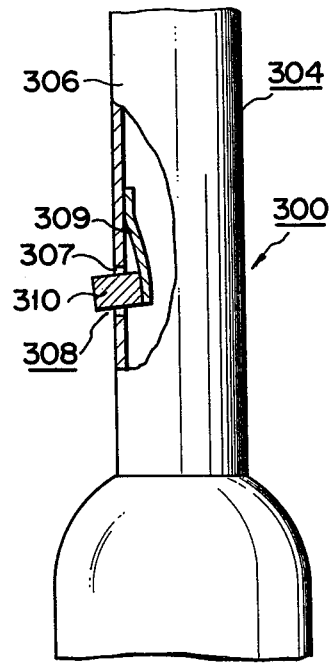

When the laser is in use and the user grasps the cylindrical body 306 of the handpiece 304, the indication member 310 is pushed into the through hole 307, as shown in FIG. 31. In response to this, the operation member 309 is deformed plastically into a curved shape. Once the laser is used, the indication member 310 of the part 300 is housed inside the through hole 307, thus indicating that the laser has been used and is no longer sterile.

Therefore, the structure of the disinfection indicator is simplified. Further, this disinfection indicator requires only a relatively small mounting space.

Figure 32:
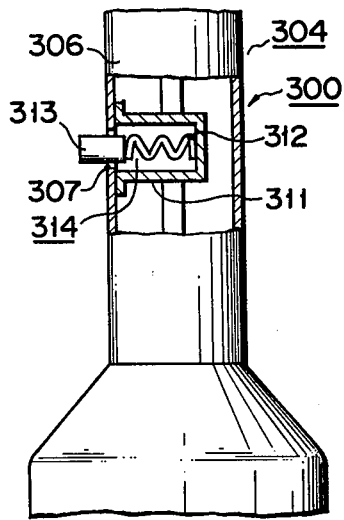
FIGS. 32 and 33 are respectively partially cutaway views of a modification of the disinfection indicator of FIG. 29 for medical equipment at different operating conditions.
Figure 33:
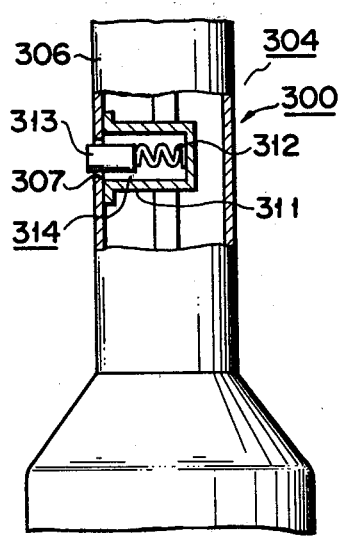

FIGS. 32 and 33 show a modification of the disinfection indicator. A cylindrical housing member 311 with a bottom is mounted in the through hole 307 formed in the cylindrical body 306 of the handpiece 304. A disinfection indicator 314 is disposed in the housing member 311. The disinfection indicator 314 comprises a coil-shaped operation member (deformable portion) 312 one end of which is fixed at the inner bottom surface of the housing member 311 and an indication member 313 which is fixed to the other end of the operation member 312. The disinfection indicator 314 is made of the shape memory alloy which shows the one-way shape memory effect when it is heated to a temperature of 50° to 100° C. or higher. When the crystal structure of the shape memory alloy is in the mother phase (high temperature phase), the coil of the operation member 312 is expanded. In this condition, the indication member 313 extends from the housing member 311 and is kept in this extending position, as shown in FIG. 32, thus indicating disinfection of the laser. Thereafter, when the handpiece 304 is in use and the cylindrical body 306 is grasped by the hand, the indication member 313 is pushed into the housing member 311, as shown in FIG. 33 and the coil of the operation member 312 is compressed and deformed plastically, thus indicating that the laser has been used and is no longer sterile.

Figure 34:
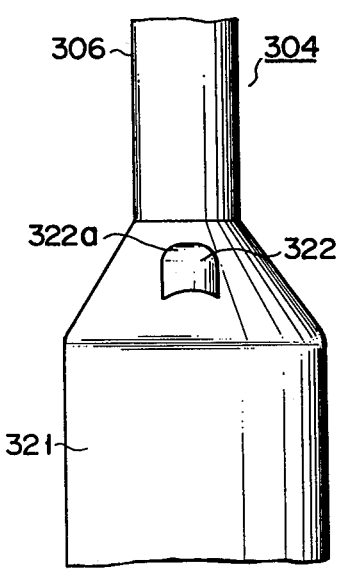
Figure 35:
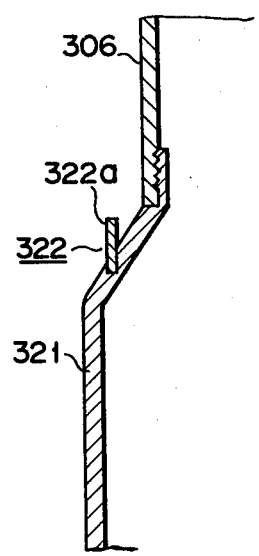
Figure 36:
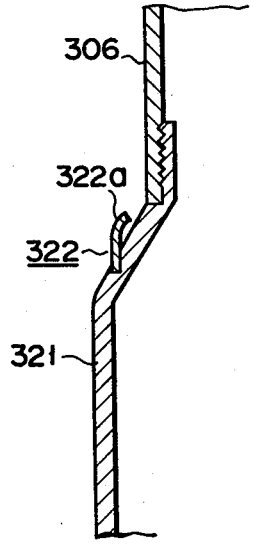

Further, in a modification of a laser of FIGS. 34 to 36, a disinfection indicator 322 is mounted on a top 321 of the handpiece 304 which is screwed in the top of the cylindrical body 306. The disinfection indicator 322 is made of the shape memory alloy which shows the one-way shape memory alloy effect when it is heated to a temperature of 50° to 100° C. or higher. When the crystal structure is modified from the martensite phase to the mother phase (high temperature phase), a deformable portion 322a is kept in a linear shape as shown in FIG. 35, indicating disinfection of the laser. Thereafter, when the handpiece 304 is used and the deformable portion 322a of the disinfection indicator 322 is bent and deformed plastically, as shown in FIG. 36, it can be visually checked that the handpiece is used and is no longer sterile.

Further, the disinfection indicator may be made of a shape memory alloy which shows a one-way shape memory effect when it is heated to a temperature of 100° to 120° C. A plurality of disinfection indicators made of shape memory alloys which are respectively modified at different temperatures may be mounted on a single device. In this case, the disinfection temperature may be measured accurately.

What we claim is:

1. A disinfection indicator mounted on medical equipment which is repeatedly used after thermal sterilization, comprising a deformable portion made of a shape memory alloy having a one-way shape memory effect, which is deformable plastically by an external force exerted as a result of use of the medical equipment, from a shape indicating disinfection of the medical equipment to an initial deformed shape which it has when the medical equipment is in use, said deformable portion being modified from the initial deformed shape to the shape indicating disinfection of the medical equipment when the medical equipment is heated to a temperature higher than a predetermined temperature, whereby it can be determined whether or not the medical equipment has been used by the shape of the deformable portion.

2. A disinfection indicator according to claim 1, wherein said deformable portion consists of a shape memory alloy which shows the one-way shape memory effect when said deformable portion is heated to a temperature higher than a temperature of 50° to 100° C. so as to restore the shape indicating disinfection of the medical equipment.

3. A disinfection indicator according to claim 1, wherein said deformable portion consists of a shape memory alloy which shows the one-way shape memory effect when said deformable portion is heated to a temperature of 100° to 120° C. so as to restore the shape indicating disinfection of the medical equipment.

4. A disinfection indicator according to claim 2 or 3, wherein said deformable portion includes a small strip, one end of which is fixed and the other end of which is a free end, and an indication member which is fixed at the other end of said small strip and indicates the initial deformed shape before disinfection and the shape indicating disinfection of the medical equipment in accordance with the deformation of said small strip.

5. A disinfection indicator according to claim 2 or 3, wherein said deformable portion has a coil, an expanded shape of which is the shape indicating disinfection of the medical equipment and a compressed shape of which is the initial deformed shape.

6. A disinfection indicator according to claim 5, further including an indication member, fixed at one end of said coil, for indicating the initial deformed shape before disinfection or the shape indicating disinfection of the medical equipment.

7. A disinfection indicator according to claim 2 or 3, wherein said deformable portion has a small strip, a linear shape of which is the shape indicating disinfection of the medical equipment and a curved shape of which is the initial deformed shape.

8. An endoscope for insertion into a channel for forceps comprising a treatment part having treatment members, and operation part, a flexible insertion member disposed between the treatment part and the operation part, a slider on said operation part and operably connected to said treatment members whereby movement of the slider causes actuation of the treatment members, and a disinfection indicator on the operation part in a moving path of the slider, said disinfection indicator comprising a deformable portion made of a shape memory alloy having a one-way shape memory effect which is deformable plastically by the slider when said slider is moved along its path to cause actuation of the treatment members, said disinfection indicator being deformed from a shape indicating disinfection of the endoscope to an initial deformed shape which it has when the slider has been moved to actuate the treatment members, said deformable portion being modified from the initial deformed shape to the shape indicating disinfection of the endoscope when the endoscope is heated to a temperature higher than a predetermined temperature, whereby it can be determined whether or not the endoscope has been used by the shape of the deformable portion.

9. An endoscope according to claim 8, wherein said deformable portion comprises a coil which is modified to an extended shape indicating disinfection of the endoscope and deformed plastically to an initial compressed shape by the movement of the slider to actuate the treatment members.

10. An endoscope according to claim 9, wherein said predetermined temperature is 50° to 100° C.

* * * * *